United States Patent
Mielzynska et al.

(10) Patent No.: US 6,890,729 B2
(45) Date of Patent: May 10, 2005

(54) DEVICE AND METHOD FOR CYTOLOGY SLIDE PREPARATION

(75) Inventors: Iwona Mielzynska, Mt. Airy, MD (US); Jay Payne, Brookeville, MD (US); James Lazar, Bethesda, MD (US)

(73) Assignee: Digene Corporation, Gaithersburg, MD (US)

( * ) Notice: Subject to any disclaimer, the term of this patent is extended or adjusted under 35 U.S.C. 154(b) by 181 days.

(21) Appl. No.: 10/153,340

(22) Filed: May 22, 2002

(65) Prior Publication Data

US 2002/0177184 A1 Nov. 28, 2002

Related U.S. Application Data

(62) Division of application No. 09/542,746, filed on Apr. 4, 2000, now Pat. No. 6,436,662.

(51) Int. Cl.[7] .......................................... G01N 33/543
(52) U.S. Cl. .................. 435/40.5; 422/55; 422/56; 422/57; 422/58; 422/101; 422/102; 422/104; 435/40.51; 435/962; 435/970; 435/973; 435/921; 435/922; 435/923; 435/924; 435/288.3; 436/174; 436/177; 436/518; 436/527; 436/531; 436/810
(58) Field of Search ..................... 422/55, 56, 57, 422/58, 101, 102, 104; 435/40.5, 40.51, 962, 970, 973, 921, 922, 923, 924, 288.3; 436/174, 177, 518, 527, 531, 810

(56) References Cited

U.S. PATENT DOCUMENTS

| | | | | |
|---|---|---|---|---|
| 4,190,314 A | * | 2/1980 | Goldsmith | 350/94 |
| 5,240,606 A | * | 8/1993 | Lapidus et al. | |
| 5,470,758 A | * | 11/1995 | Hayes | 436/177 |
| 5,471,994 A | * | 12/1995 | Guirguis | 128/760 |
| 5,494,828 A | * | 2/1996 | Leopando | 436/180 |
| 5,589,400 A | * | 12/1996 | Hayes | 436/177 |
| 6,300,140 B1 | * | 10/2001 | Robinson | 436/518 |
| 6,436,662 B1 | * | 8/2002 | Mielzynska et al. | 435/40.5 |

OTHER PUBLICATIONS

Sawaya et al., Aug. 1999, "New Technologies in Cervical Cytology Screening: A Word Of Caution", Obstetrics & Gynecology, 94(2):307–310.

Lee, et al., Aug. 1997, "Comparison of Conventional Papanicolao Smears and a Fluid–Based, Thin–Layer System for Cervical Cancer Screening", Obstetrics & Gynecology, 90(2):278–284.

Oud, et al., 1986, "Automated deposition of celluar material on glass slides: Cytopress", Acta histochemica, Suppl.–Band XXXII, S. 209, pp.209–214.

Evidence Report/Technology Assessment No. 5,1999, "Evaluation of Cervical Cytology", AHCPR Publication No. 99–E010.

Bosanquet et al., Apr. 24, 1999, "Assessment of automated primary screening on PAPNET of cervical smears in the PRISMATIC trial", The Lancet, 353:1381–1375.

Office Depot 2000 Catalog p. 323.

* cited by examiner

Primary Examiner—Christopher L. Chin
(74) Attorney, Agent, or Firm—Morgan & Finnegan, L.L.P.

(57) ABSTRACT

This invention provides a novel device and method for preparing cytology slides. The device comprises a book-like form including an absorbent material and filter attached to the inside surface of a front cover and a cytology slide removeably attached to an inside surface of a back cover. A sample is removed from the body of a patient, placed in a liquid-based solution, and then on the filter. When the book-like form is closed, the sample is effectively transferred to the slide.

11 Claims, 8 Drawing Sheets

(2 of 8 Drawing Sheet(s) Filed in Color)

DEVICE AND METHOD FOR CYTOLOGY SLIDE PREPARATION

This is a divisional of application Ser. No. 09/542,746 filed Apr. 4, 2000 issued as U.S. Pat. No. 6,436,662 B1 on Aug. 20, 2002.

FIELD OF INVENTION

The present invention relates generally to the preparation of cytology slides and, more particularly, to a device and associated method for preparing cytology slides.

BACKGROUND OF THE INVENTION

Cytology slides are prepared to screen and diagnose cellular samples taken from, for example, tissue samples, samples from the uterine cervix, urine, sputum, blood, fine needle aspiration biopsy, urethral, bronchial brushings and washings, cerebral spinal fluid, and other body fluids. The reliability and efficacy of the screening methods of these slides are measured by their ability to diagnose infections, precancerous lesions or cancerous lesions while at the same time avoiding false positive or negative diagnosis. The reliability of these slides is a primary issue. Often, the results are not accurate or are unreadable. Thus, there is a constant effort to improve the reliability and efficacy in the preparation of cytology samples.

One of the most common uses of cytology slides is for screening and diagnosis of a cervical sample. Carcinoma of the cervix is one of the most common malignancies in women, causing nearly 5,000 deaths per year in the United States. Approximately 60% of these cases are associated with absent or deficient screening. Approximately 25% of the screening failures are the result of errors in cervical sampling or smear interpretation.[1]

Screening for precancerous or cancerous changes of the uterine cervix traditionally involves microscopic assessment of cervical Papanicolaou smears, called Pap smears. This traditional method for screening requires scraping a woman's cervix with a sampling device, such as a cotton applicator stick, spatula or brush, and smearing this sample onto a slide for review by a medical lab professional. The specimen is gently spread across a slide to evenly distribute the cell sample. The slide is then fixed, stained, and examined under a light microscope for cellular abnormalities.

In carrying out this operation, the portion of the cell sample that is smeared onto the slide may contain blood, mucus, inflammatory cells, and clumps of cells. Accurate interpretation of up to 40% of conventional Pap smears are compromised by the presence of blood, mucous, obscuring inflammatory cells, scant cellular material and air-drying artifacts.[2] The presence of these contaminants can obscure many of the cells, causing important precancerous lesions to be missed when the slide is reviewed at the lab or, alternatively, making the entire slide unreadable.

One of the problems with the conventional Pap smear is how quickly the sample dries out once it is smeared on the slide. With a conventional Pap smear, the sample must be fixed immediately in order to avoid the drying out of the cells, which ruins the sample.

Another problem with the conventional Pap smear is the frequent inaccuracy of the test result. Common inaccuracies include both false positive and false negative Pap test results. A false positive Pap test occurs when a patient is told she has abnormal cells when the cells are actually normal. A false positive result may require a woman to undergo unnecessary and costly medical procedures. A false negative Pap test result occurs when a specimen is called normal, but the woman has a lesion. A false negative Pap test may delay the diagnosis and treatment of a precancerous or even a cancerous condition.

The conventional Pap smear has false negative rates ranging from 10–50%, with up to 90% of those false negatives due to limitations of sampling or slide preparation.[3] To decrease false negative rates associated with interpretation error, re-screening a portion of the negative smear or recalling the patient for another sample is required.

Concern over the frequency of false-negative results of the traditional Pap smear has led to the development of a variety of other technologies or clinical strategies, such as liquid-based cytology systems, to improve Pap testing. For example, the Cytyc, Inc. (Marlborough, Mass.), ThinPrep® and the TriPath, Inc. (Burlington, N.C.), CytoRich® Pap test systems are two commercially available, FDA approved fluid-based methods used for the collection and preparation of cervicovaginal samples.

With the ThinPrep® system, a gynecologic sample is collected in the same manner as the conventional Pap test using a broom-type device or plastic spatula and endocervical brush combination, but rather than smearing the cytological sample directly onto a microscope slide, this method suspends the sample cells in a fixative solution (i.e. PreservCyt®). The ThinPrep® slide preparation system uses an automated apparatus called a Cytyc 2000® that involves filtration using vacuum pressure and positive pressure-transfer steps to prepare cytology slides.[4]

With the CytoRich® slide preparation system, the gynecologic sample is also collected in the same manner as the conventional Pap test. Like the ThinPrep® system, the CytoRich® system also places the sample in a liquid medium for further purification prior to analysis. CytoRich® specimens are processed using two centrifugation steps through a gradient solution to separate the diagnostic cells from the interferring material. The cells are ultimately re-suspended in a final preparation that is applied to the slide using a special pipetting apparatus (Autocyte Prep System®) provided by the manufacturers (Tripath, Inc.). This transfer step can also be performed manually. Thereafter, a sample is placed on a slide and analyzed by cytology.

These new methods have demonstrated increased quality in the preparation of the sample, improved detection rates, and a reduced need for patients who must return for repeat smears. However, in both the ThinPrep® and the CytoRich® slide preparation systems, a time consuming and expensive procedure is followed to prepare a mono-dispersed layer of cells on a cytology slide.

Although each of these systems reduces significantly the false-negative rate of the traditional Pap smears, the health care market has been slow in adopting these systems because of their cost and preparation time compared to the conventional Pap smears.

SUMMARY OF THE INVENTION

The invention provides a device and a method of using the device that overcomes these problems. The device and associated method provide a better quality prepared cytology slide having a more even distribution of cells with less interference from debris than the conventional Pap method, while offering an easier, quicker and more economical procedure as compared to known liquid-based medium methods. Thus the device and associated method facilitate the preparation and screening process of cytology slides.

According to one embodiment, a device for facilitating the preparation of cytology slides comprises a first cover having an inside surface, a second cover having an inside surface and an interposed spine. The spine may be replaced by one or more hinges. The first and second cover are pivotably secured to the spine so as to be foldable into a book form capable of an open and closed position. An absorbent material is mounted on the inside surface of the first cover and a filter overlays the absorbent material. The cytology slide is removeably mounted to the inside surface of the second cover. The slide is positioned on the inside surface of the second cover to contact with the filter when the book-like device is in the closed position.

In another aspect, the invention is directed to a method of preparing cytology slides. The method comprises combining a cellular sample with a liquid-based medium to create a solution, mixing the solution, extracting the sample or an aliquot of the sample from the solution and providing a slide preparation device. The device comprises a first cover having an inside surface, a second cover having an inside surface and an interposed spine. The first and second cover are pivotably secured to the spine so as to be foldable into a book form. An absorbent material is mounted to the inside surface of the first cover and a filter overlays the absorbent material. A slide is removeably mounted to the inside of the second cover so that the filter contacts the slide when the device is in the closed position. The method further comprises applying the sample to the filter, closing the book form so that the filter containing the sample contacts the slide, and applying a pressure to the contact surface to effectively transfer the specimen to the slide. The range of pressures appropriate for the absorbent matter and the filter in the device is provided by the design of the device. In this way, a cytology slide containing an evenly distributed number of cells is prepared quickly and reliably.

BRIEF DESCRIPTION OF THE DRAWINGS

The patent file contains at least one drawing executed in color. Copies of this patent with color drawing(s) will be provided by the Office upon request and payment of the necessary fee.

DETAILED DESCRIPTION OF THE PREFERRED EMBODIMENTS

Hereinafter, the invention will be described in greater detail with reference to the preferred embodiments. However, it is understood that the device and associated method of the invention are applicable for the preparation of cytology slides for any cellular or tissue samples, preferably clinical cellular samples, known in the art.

Figure 1A:
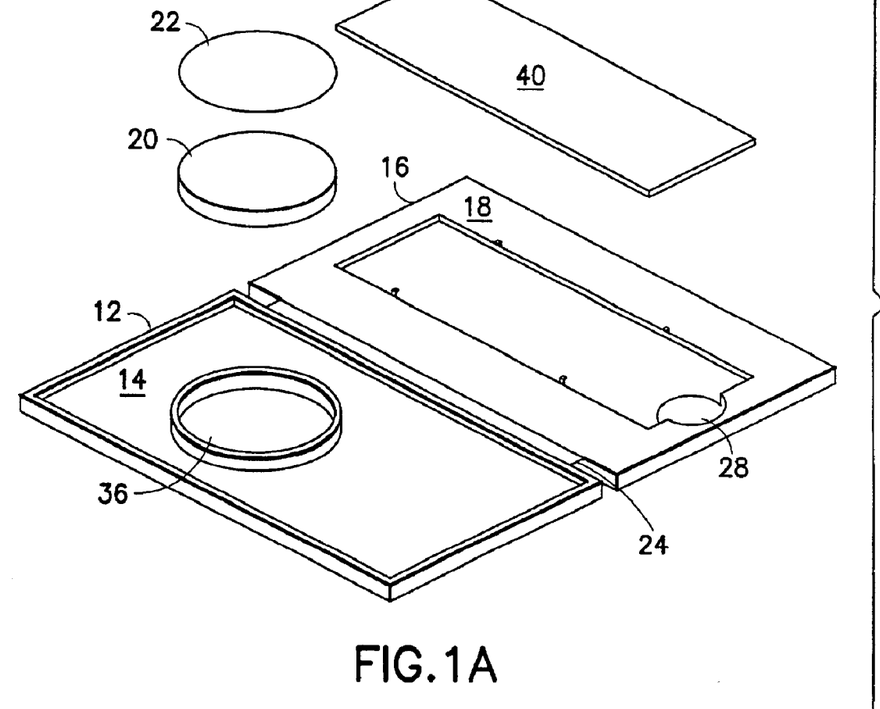
FIG. 1A is an exploded view of one embodiment of the devices.

Referring now to FIG. 1A, in one embodiment of the invention, a kit 100 for facilitating the preparation of cellular samples includes a device 10 comprising a front cover 12, a rear cover 16, and a spine 24 connecting the front and rear covers 12, 16. The spine 24 spaces the front cover 12 and the back cover 16 when folded in the closed position and creates a book-like form, wherein the inside 14 of the front cover 12 and the inside 18 of the back cover 16 face and contact against each other. In an alternative embodiment illustrated in FIG. 1A, the front cover 12 does not need to be the same size as the back cover 16.

The covers 12, 16 and spine 24 may be made of a single piece of flexible material. Such flexible material can include, for example, cardboard or some flexible plastics to which a controlled pressure may be applied to the outside covers 12, 16 without puncturing or cracking the covers. The material should not absorb the sample or solution applied to the filter 22 and absorbent material 20 (described in more detail below). The material should also be selected to enable various users, such as, for example, lab technicians and doctors, to apply consistent or controlled amount of pressure to prevent over squeezing the solution, resulting in spillage or distortion of the morphology of the sample by the exertion of too much pressure.

Figure 2A:
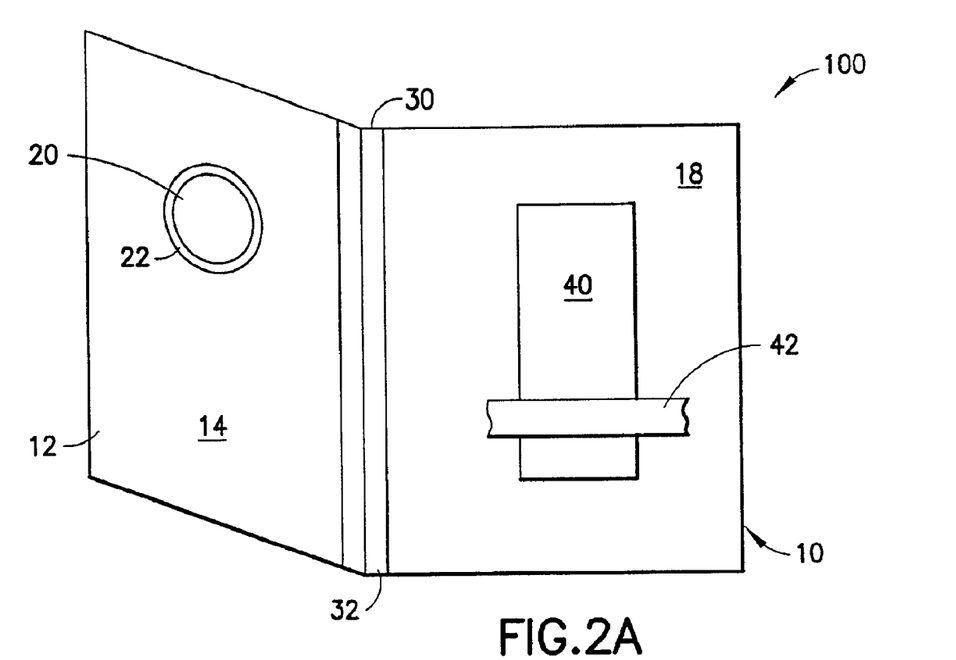
FIG. 2A is an isometric view of another embodiment of the device illustrating a single continuous hinge.
Figure 2B:
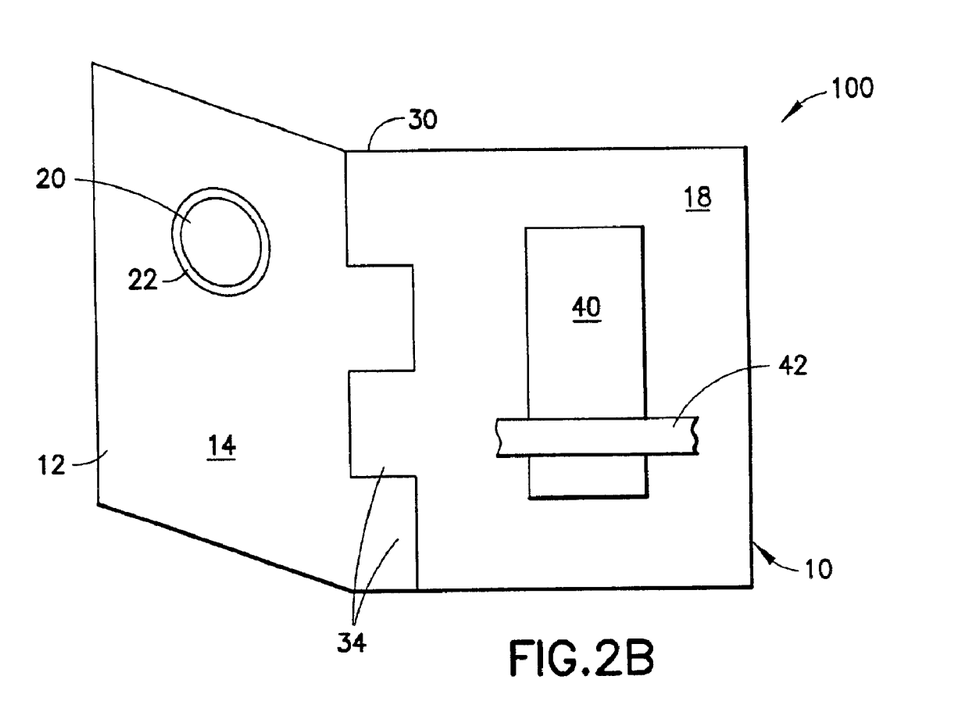
FIG. 2B is an isometric view of one embodiment of the device illustrating a hinge having a number of interlocking pieces 34.

Alternatively, the device 10 can be made from an inflexible material. Such inflexible material can include, for example, wood, wood-derived materials, metals or inflexible plastics. When inflexible materials are used for the front and back covers, it may be preferable to use one or more hinges to connect the front and back covers. In the embodiment illustrated in FIGS. 2A and 2B, a hinge 30 connects the front cover 12 and back cover 16. The hinge 30 is constructed so that the front cover 12 and back cover 16 face and contact each other when the book form is in the closed position. The hinge 30 can be one single, continuous piece 32 (FIG. 2A) or, alternatively, a number of flexible or interlocking pieces 34 (FIG. 2B).

Figure 1B:
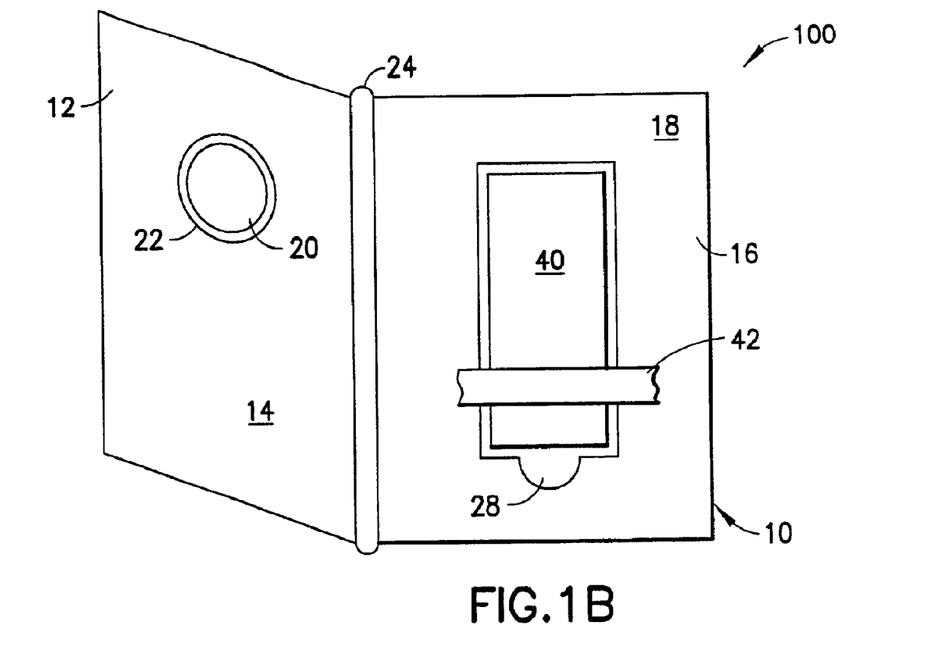
FIG. 1B is an isometric view of one embodiment of the device.

In FIG. 1B, the device is shown in the open position. Front cover 12 is flipped open, exposing an absorbent material 20 and a filter 22 attached to the inside 14 of the first cover 12. A slide 40 is also shown mounted to the inside 18 of the back cover 16 of the device 10.

The absorbent material 20 is hydrophilic in nature. In particular, the absorbent material is absorbent to both water and alcohol-based solutions and is preferably uniform in its absorbency. The absorbent material is preferably inert and stable so as not to react with the alcohol solution or components of the cellular sample. The absorbent material preferably possesses stability properties enabling the finished device to be stored for several years. Standard filter papers or blotting papers may be used as an absorbent material. For example, one suitable absorbent material is that sold by Bio-Rad® (Hercules, Calif.) called Bolt Absorbent Filter Paper (Extra Thick) consisting of 100% cotton fiber. Alternatively, the absorbent material can be 100% double-sided, twill-pattern wovencotton (e.g. Wipers Natural; TX306 made by TexWipe® Company), or polyvinyl acetal foam (HydroSponge™; TX5390 made by Tex Wipe® Company), Gelman's® Absorbent Pad, Cellulose Fiber Filter Pad, Whatman's® Glass Microfibre filters, Whatman's® cellulose paper, TexWipe® Company (Upper Saddle River, N.J.) trademarked Absorbond® (Wipers Synthetic; TX404) consisting of 100% hydro-entangled polyester, Denville® Scientific Hyblot Mater, Milipore® cellulose absorbent pads or any other absorbent material or combination of materials known in the art.

The absorbent material 20 adheres to the inside 14 of the front cover 12 by, for example, an adhesive or, alternatively, by a heat spot weld. It should be understood that the adhesive is selected so as not to interfere with the properties of the absorbent material, as mentioned above. One such suitable adhesive is gel cyanoacrylate sold by Loctite under the trademark Loctite 4541®. Alternatively, the adhesive can be hot melt or acrylic or synthetic rubber based adhesives or any adhesive known in the art.

The filter 22 overlays the absorbent material 20. Any filter known in the art can be used. The filter 22 is preferably a polycarbonate film containing approximately 3 to 8 micrometer pores. The pore sizes can be varied to enable the filter to capture the desired cells on the surface of the filter while allowing the debris to pass through to the absorbent material 20. The filter should also be inert, stable, and alcohol resistant. Alternatively, the filter can be nylon, cellulose, polyester, teflon, polytetrafluorethylene or any other filter material known in the art.

An adhesive to attach the filter 22 to the absorbent material 20 is selected so as not to interfere with the sample placed on the filter 20. Revertex Chemicals Ltd. (Malaysia) sells some suitable adhesives for attaching the filter 22 to the absorbent material 20, such as, for example, starch, dextrin, latex and casein. Alternatively, the adhesive can be ethylene vinyl acetate and polyvinyl acetate emulsion adhesive for lamination of the filter 22 and the absorbent material 20. In other embodiments, the filter 22 can be held in proximity to the absorbent material 20 by mechanical means, such as, for example, a rim of plastic to hold the overlapping filter 22 onto the absorbent material 20 disk.

The slide 40 is a standard slide, made of either glass or plastic, commonly used in cytology. In the embodiment of FIG. 1A, the slide 40 is mounted to the inside 18 of the back cover 16 in such a way that enables the slide 40 to be easily removed. In the embodiment of FIG. 1B, the slide 40 is mounted to the inside 18 of the back cover 18 by a piece of adhesive or tape 42. However, any commonly known method known in the art that accomplishes this goal can be used to mount the slide. For example, the slide 40 can be press-fit into a cutout portion 44 of the inside 18 of the back cover 16, held by Velcro® strap, or placed in a pocket 46 formed in the inside 18 of the back cover 16 (FIG. 3) to facilitate removal of the slide 40.

Figure 1C:
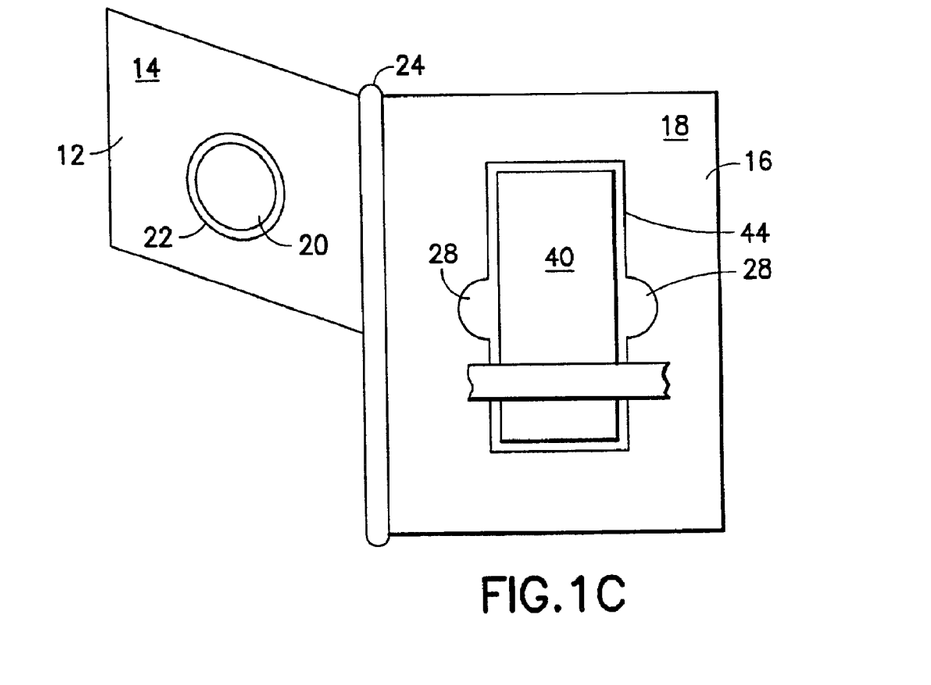
FIG. 1C is an isometric view of one embodiment of the device.

In another embodiment, the inside 18 of the back cover 16 includes finger recesses 28 to aid a user in lifting the slide 40 out of the back cover (FIGS. 1B and 1C). The finger recesses 28 should be positioned away from the preparation area to avoid contamination of the transferred sample.

The absorbent material 20 with the attached filter 22 are positioned on the inside 14 of the front cover 12 of the book-like device 10 so that when the book-like device 10 is closed, the filter 22 contacts a central location on the slide 40.

Figure 4A:
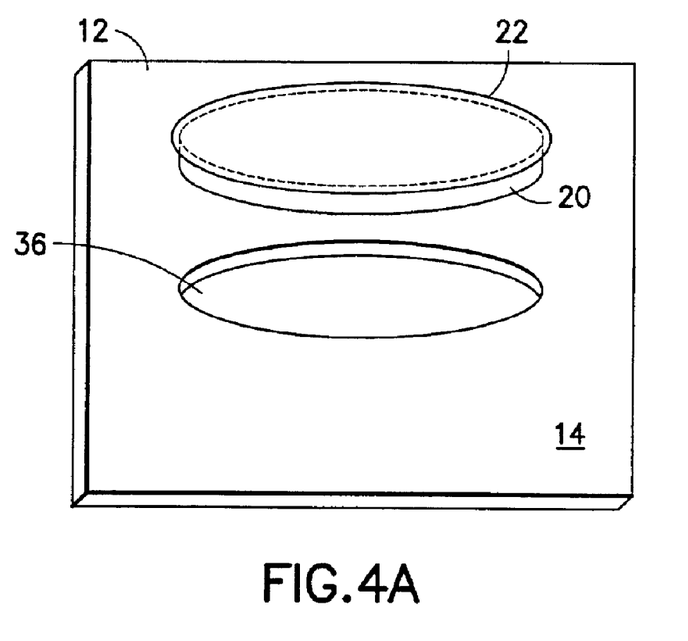
FIG. 4A is a partial view of the front cover of one embodiment of the device illustrating the recess or well 36.
Figure 4B:
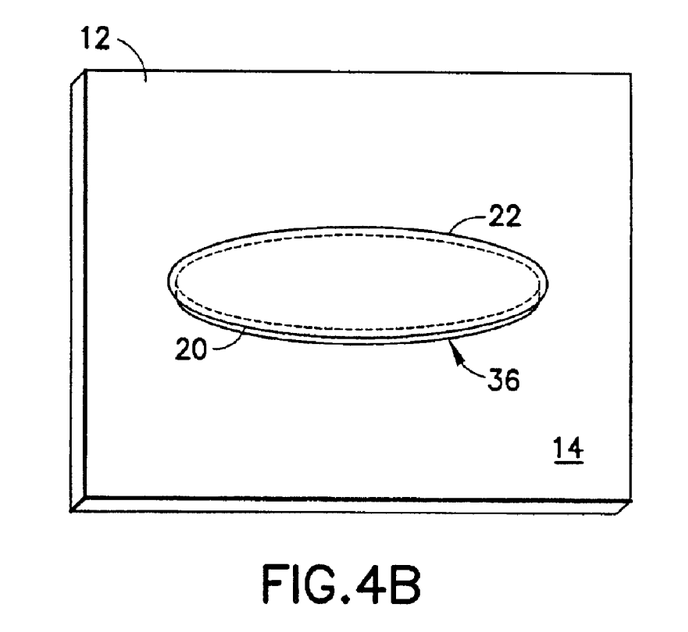
FIG. 4B is a partial view of the front cover of one embodiment of the device illustrating the absorbent material and filter extending above the inner surface.
Figure 5:
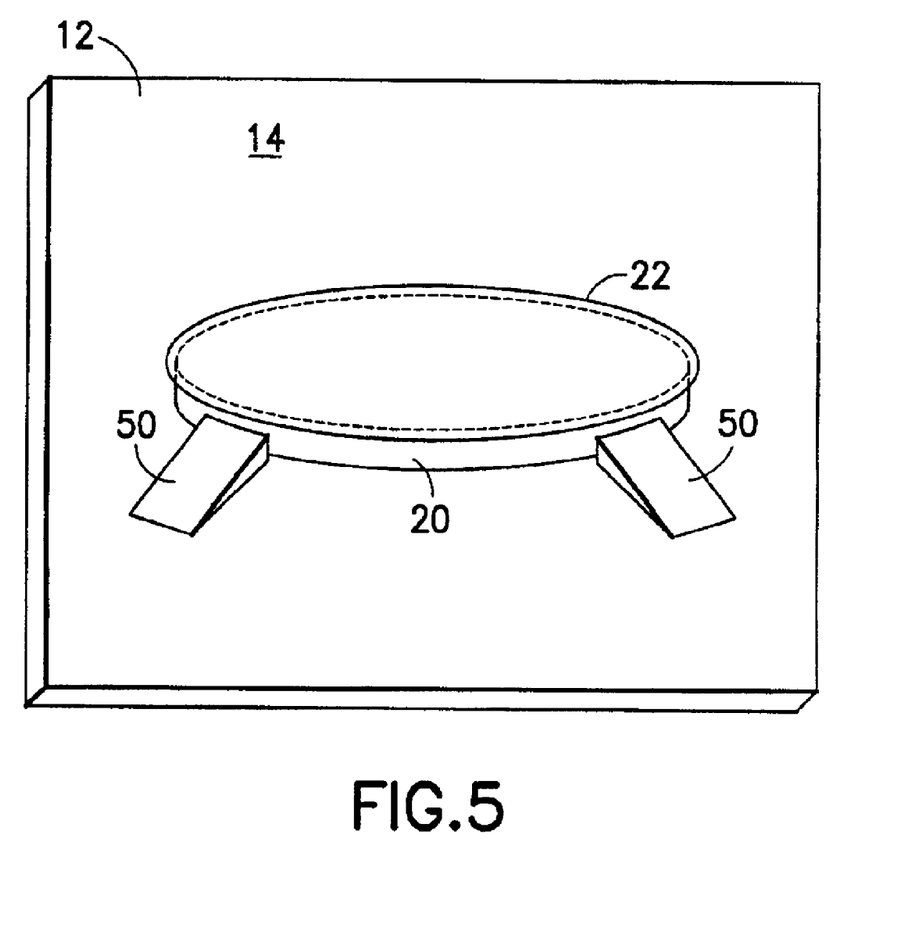
FIG. 5 is a partial view of the front cover of one embodiment of the device illustrating a plurality of supports 50.

In another embodiment, as illustrated in FIGS. 4A and 4B, the absorbent material is placed in a recess or shallow well 36 formed in the inside 14 of the front cover 12 so that the upper portion of the absorbent material 20 having the overlaying filter 22 (as will be described in more detail below) extends above the inside surface 14 of the front cover 12. This recess or shallow well 36 provides the added benefit of holding any excess solution that escapes from the bottom of the absorbent material 20. In yet another embodiment, the absorbent material 20 is held in place on the inside 14 of the front cover 12 by a plurality of supports 50, as illustrated in FIG. 5.

When the book-form is closed, the inside 14 of the front cover 12 and the inside 16 of the back cover 10 contact each other. In the embodiment in which the upper portion of the absorbent material 20 and filter 22 extend above the inside surface 14 of the front cover 12, there is no need to exert an additional pressure to transfer the sample to the slide 40 from the filter 22, when the back cover 10 comes into contact with front cover 12. The slide 40, which can be flush with the inside 18 of the back cover 16 will compress the absorbent material 20 and filter 22, thus transferring the sample to the slide 40.

Figure 3:
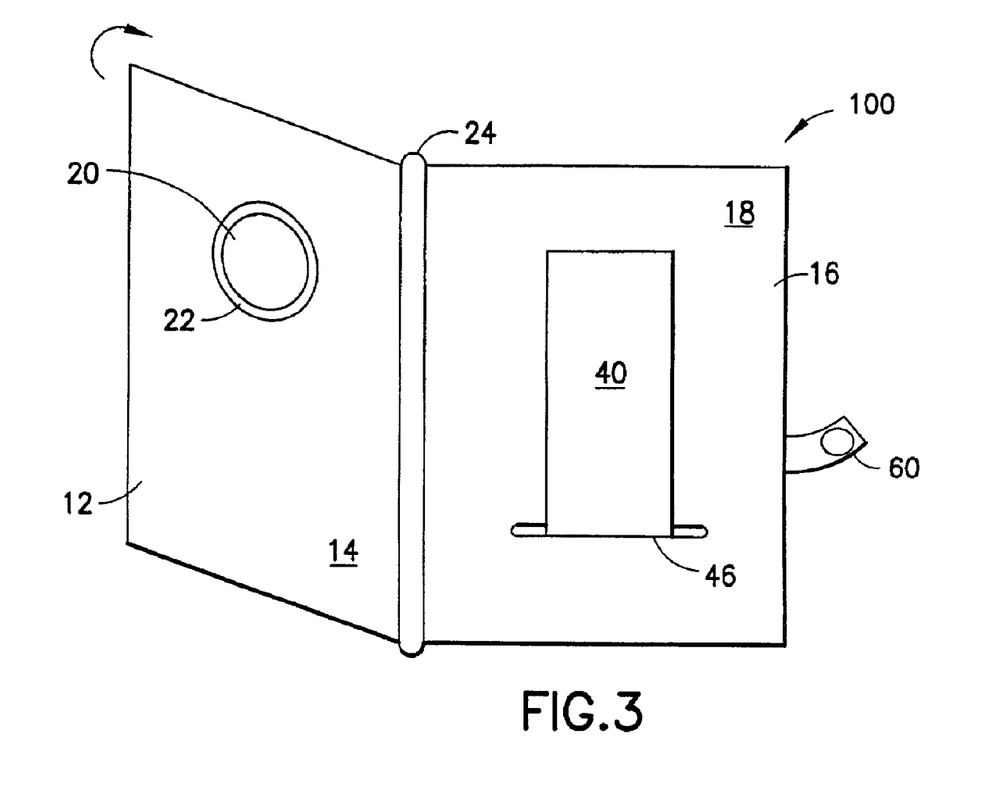
FIG. 3 is an isometric view of another embodiment of the device illustrating a pocket 46 and fastening means 60.

As illustrated in FIG. 3, the kit 100 may optionally include a mechanical fastening means 60 to lock together and maintain the contact of the inside surfaces 14, 18 of the front and back covers 12, 16, respectively, when the book-form device 10 is closed. Any mechanical fastening means known in the art, such as Velcro®, tape, clasps, snaps, or the like, can be used. When the book-form device 10 is closed, causing the filter 22 to contact the slide 40, the appropriate amount of controlled pressure may be applied by fastening the fastening means 60. In an embodiment including a clasp or snap fastening means 60, an audible snap is preferably heard when the fastening means is fastened. This audible snap informs the user that a controlled amount of pressure is being applied to transfer the sample from the filter 22 to the slide 40.

A cellular sample is any cellular or tissue specimen collected from a subject for the purposes of screening or diagnosing, commonly known in the art, that is capable of being suspended in a liquid-based medium. Such samples are obtained, for example, from the cervix, the throat, urine sediments, lymph nodes, esophagus, bronchial, breast (i.e. nipple discharge), skin lesions, thyroid, blood and disruptive tissue biopsies.

In the present invention, the kit 100 is used to prepare a cytology slide with a mono-dispersed cell sample. In the broader aspects of the invention, there is no limitation on the collection and handling of samples as long as consistency is maintained. The cell or tissue sample is obtained by methods known in the art, such as, biopsies, surgical resections, standard bodily fluid collection techniques or the like.

In an embodiment in which the cellular sample is a cervical smear, the sample is taken from the cervix. The present invention employs standard techniques for collecting cervical cells; for example, it generally involves the insertion of a cervical brush or broom device and the taking of cells from the surface of the cervix and the endocervix.

The cellular sample is preferably placed in any liquid-based cytology medium used and known in the art. One example of such a cytology medium is known as a Universal Collection Medium (UCM) from Digene Corp. (Gaithersburg, Md.). UCM is a cell collection medium which preserves both cell morphology and cellular biomolecules for quantitative analysis in a cell sample so that multiple assays can be carried out from a single patient sample.[5] Other liquid-based cytology media can be used, such as PreservCyt® from Cytyc, Inc. (Boxborough, Mass.) and CytoRich® Preservative Fluid from TriPath, Inc. (Burlington, N.C.).

One preferred method places the cellular sample in 1 milliliter of UCM. This solution is then suspended, by mixing. Mixing can be conveniently achieved, for example by vortexing the solution for approximately five to ten seconds.

After suspending the cells, a sample is removed carefully, usually with a pipette, and placed on the filter 22. If one milliliter of UCM is used, it may be preferable to use an aliquot of approximately 200 microliters from the solution. This sample is then applied to the surface of the filter 22. One skilled in the art understands that other liquid media may be used and the sample may be suspended in varying amounts of such media. The solution and other debris pass through the filter 22 to the absorbent material 20 while the cells are captured on the surface of the filter 22. The book-like device 10 is then closed so that the filter 22 contacts the slide 40 for about 15 seconds while a moderate pressure, created when the covers are closed and locked together, is applied to the front and back covers 12, 16, respectively. The device applies from 200 to 1000 grams of pressure to the slide and specimen for optimum transfer of the cytology specimen to the slide.

The pressure applied to the covers 12, 16 transfers the cells captured by the filter 22 to the slide 40. After the pressure is applied, the slide 40 can be removed from the book-like device 12 and fixed and stained in the routine manner.

In order to optimally preserve the cell detail and maintain the morphologic characteristics, without distortion, the cells are preferably wet-fixed before any air drying occurs.

Conventional methods known in the art can be used for fixing, staining and analyzing the sample. The following provides a general outline of such conventional techniques but should not be construed to limit the applicability of the invention to the alternative cytology preparation techniques known in the art.

Most laboratories use a 95 percent ethanol solution for most routine preparations that require fixations. However, other fixatives known in the art can be used. Most of these fixatives are composed of polyethylene glycol in an alcohol base and are applied either from a dropper bottle or in spray form. Coating fixatives are also widely used for cervical smears. These fixatives cover the sample in—a waxy coating that protects it from damage.

One advantage of using the absorbent material 22 is that the cell sample will not dry out as quickly. When the book-like device 10 is closed, the absorbent material 22 keeps the sample moist as it is transferred to the slide since an liquid-based solution is used and the absorbent material 20 is held in close physical proximity to the specimen. The device 10 maintains a "moist" or "humid" environment so that the cells can be preserved in the device 10 before fixing for up to 30 minutes following application on the slide 40. Once on the slide 40, the cell sample should be preserved as mentioned above.

After the cells are transferred to the slide and the cells are fixed, the cellular sample is generally stained. Staining may be required to retain the transparency of the cells and display variations of cellular maturity and metabolic activity. Any stain or staining method known in the art can be used.[6] The universal stain for cytological preparations is the Papanicolaou stain. Although, any stain known in the art, such as Hematonylin and Eosin stain or special chemical stains or immunochemical stains, can be used.

Once any staining technique has been completed, the slide may be mounted in a suitable medium satisfactory for microscopy. There are many commercially available mountants that can be used that are well known in the art. These mountants protect the sample from dust and damage and should harden rapidly and not discolor or crystallize during long-term storage.

A coverslip may then be placed over the sample. Coverslipping has traditionally been achieved using a thin glass slip (less than 0.17 millimeters) or continuous film. Various sizes are commercially available but the entire sample preparation should be covered by the mountant and the coverslip.

EXAMPLE

Comparison with Conventional Pap Smear

Figure 6A:
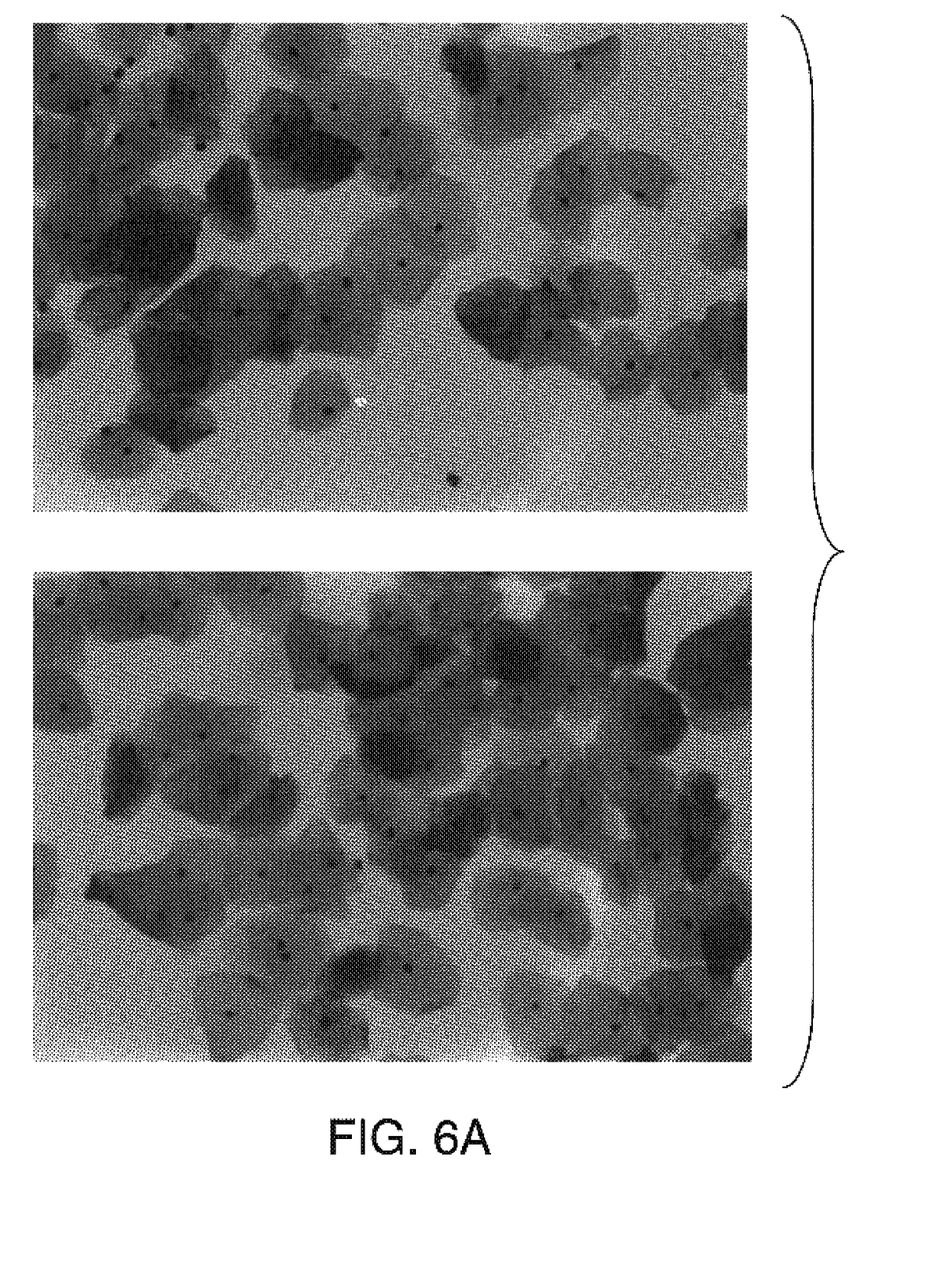
FIG. 6A illustrates the cell distribution of a cervical sample using the device and method of the present invention.

A cervical sample was taken from a female patient and placed in a one milliliter of Universal Collection Medium.[7] An aliquot of 200 microliters is extracted from the solution and applied to the surface of the filter 22 of the book-form device 10. The book-form device 10 was closed for approximately 15 seconds while a controlled amount of pressure was applied. The slide 40 was then removed from the book-form device 10 and the sample was fixed, stained and placed under a light microscope. FIG. 6A shows the morphology of cervical cells prepared by the method of the present invention.

Figure 6B:
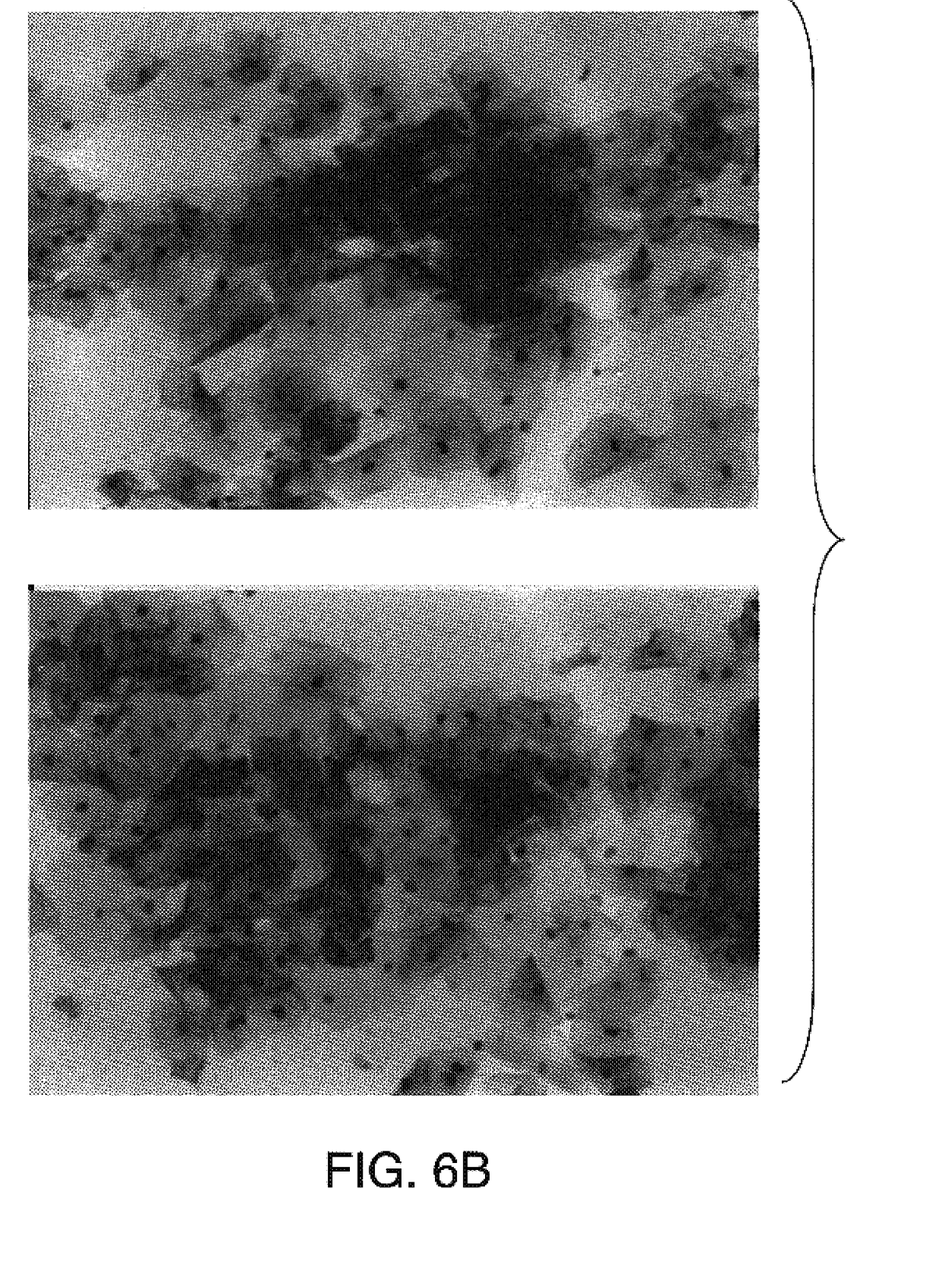
FIG. 6B illustrates the cell distribution of a conventional Pap smear (archival) at a magnification of ×120.

FIG. 6B was taken from archived routine Pap smears to show the morphology, distribution of cells and staining of stored samples fixed to slides for comparison. The morphology of the cells prepared by the method of the present invention shows better quality and more evenly distributed cells with less interference from debris than the conventional Pap smear.

Table 1, below, shows a comparison of Pap slides from the same patients made with the conventional Pap smear technique and the UCM book-form device Pap slide technique. These results demonstrate complete agreement between the two procedures.

TABLE 1

| UCM vs. Conventional Pap* | | |
|---|---|---|
| Case ID | Conventional Pap | UCM Manual Pap |
| 1W | WNL | WNL |
| 2W | LSIL | HSIL |
| 3W | WNL | WNL |
| 4W | WNL | WNL |
| 5W | WNL | WNL |
| 6W | WNL | WWL |
| 7W | WNL | WNL |
| 8W | WNL | WNL |
| 9W | WNL | WNL |
| 10W | WNL | WNL |
| 11W | WNL | WNL |
| 12W | WNL | WNL |
| 13W | WNL | WNL |
| 14W | WNL | WNL |
| 15W | WNL | WNL |

100% Agreement
Key:
WNL-Within Normal Limits
LSIL-Low-grade Squamous Intraepithelial Lesions
HSIL-High-grade Squamous Intraepithelial Lesions
ASCUS-Atypical Squamous Cells of Undetermined Significance It will be apparent to those skilled in the art that various modifications and variations can be made in the device and method of the present invention without departing from the spirit or scope of the invention. Thus, it is intended that the present invention embraces all such modifications and variations within the spirit and scope of the appended claims.

All articles, patents or other references cited or referred to herein are hereby incorporated herein in toto by reference.

REFERENCES

[1] Sawaya, George F. (M.D.), Grimes, David A. (M.D.), "New Technologies in Cervical Cytology Screening: A Word Of Caution", Obstetrics and Gynecology, 1999, Vol. 94, pg.1, which is incorporated herein by reference.

[2] Davey D D, Nielsen M L, Rosenstock W, Tilde T S. "Terminology and specimen adequacy in cervicovaginal cytology: The College of American Pathologists interlaboratory comparison program experience", Arch. Path. Lab. Med. 1992, vol. 116, pgs. 903–907 which is incorporated herein by reference.

[3] van der Graaf Y, Vooijs G P, Gaillard H L J, Go DMDS, "Screening errors in cervical cytological screenings", Acta Cytologica, 1987, vol. 31, pgs. 434–8;
Dehner L P, "Cervicovaginal cytology, false-negative results, and standards of practice", Am. J. Clin. Pathol, 1993, vol. 99, pgs. 45–47;
Gay J D, Donaldson L D, Goetliner J R., "False negative results in cervical cytologic studies", Acta Cytologica, 1985, vol. 29, pgs. 1043–1046; and Morell, N D, Taylor J R, Snyder R N, Ziel H K, Saltz A, Willis S., "False-negative cytology rates in patients in whom invasive cerviocal cancer subsequently developed", Obstet. Gynecol., 1982, vol. 60, pgs. 41–45 which are incorporated herein by reference.

[4] Further information about the operation and efficiency of the ThinPrep® method is set forth in Obstetrics & Gynecology, Vol. 90, No. 2, pps. 278–284 in an article by Lee, Ashfaq, Birdsong, Corkill, McIntosh and Inhorn titled "Comparison of Conventional Papanicolaou Smears and a Fluid-Based, Thin-Layer System for Cervical Cancer Screening" which is incorporated herein by reference.

[5] Further information about the UCM is set forth in PCT International Application No. PCT/US98/26342 (European patent application number 98962066.1), filed on Dec. 11, 1998 by Attila T. Lorincz and Yanlin Tang for a Universal Collection Medium which is incorporated herein by reference.

[6] Further information about fixation and staining methods and materials used is provided by the Health Care Financing Administration and set forth in "The Tutorial of Cytology" by Wied, Keebler, Koss and Reagan (1998, pps. 580–583), and in "Comprehensive Cytopathology" by Bibbo, (1991, pps. 882–892) which are incorporated herein by reference.

[7] Further information about the UCM is set forth in PCT International Application No. PCT/US98/26342 (European patent application number 98962066.1), filed on Dec. 11, 1998 by Attila T. Lorincz and Yanlin Tang for a Universal Collection Medium which is incorporated herein by reference.

We claim:

1. A device for facilitating the preparation of cytology slides, the device comprising:
    a first cover having an inside surface;
    a second cover having an inside surface, the second cover hingeably attached to the first cover so as to be foldable into a book form capable of an open and closed position;
    an absorbent material mounted on the inside surface of the first cover;
    a filter, the filter overlays the absorbent material; and
    a cytology slide, wherein the cytology slide is mounted to the inside surface of the second cover, the slide being positioned on the inside surface of the second cover to contact with the filter when the book form is in the closed position.

2. The device of claim 1, wherein the filter is polycarbonate.

3. The device of claim 1, wherein the absorbent material is a polyvinyl acetal foam.

4. The device of claim 1, wherein the absorbent material is 100% cotton fiber.

5. The device of claim 1, wherein the first cover is hingeably attached to the second cover by a hinge comprising a single, continuous piece.

6. The device of claim 1, wherein the first cover is hingeably attached to the second cover by a hinge comprising a plurality of interconnected pieces.

7. The device of claim 1 wherein the slide is removably mounted to the second cover.

8. The device of claim 1 wherein the first cover is hingeably attached to the second cover by a spine interposed between the first and second covers.

9. A method of preparing cytology slides, the method comprising:
    providing a slide preparation device comprising a first cover having an inside surface, a second cover having an inside surface, said first and second cover hingeably secured to each other so as to be foldable into a book form, an absorbent material mounted to the inside surface of the first cover, a filter overlaying the absorbent material and a slide attached to the inside surface of the second cover;
    applying an aliquot to the filter; and
    closing the book form so that the filter containing the aliquot contacts the slide.

10. The method of claim 9, wherein the aliquot comprises a cellular sample in a liquid-based medium.

11. The method of claim 9, further comprising applying pressure to the first and second covers after closing the book form.

* * * * *